United States Patent [19]

Werle et al.

[11] Patent Number: 5,696,052
[45] Date of Patent: Dec. 9, 1997

[54] METHOD AND COMPOSITION FOR COMBATTING MICROBIAL, VEGETABLE AND ANIMAL PESTS WITH ACROLEIN

[75] Inventors: Peter Werle; Martin Trageser, both of Gelnhausen; Oswald Helmling; Harald Jakob, both of Hasselroth, all of Germany

[73] Assignee: Degussa Aktiengesellschaft, Frankfurt am Main, Germany

[21] Appl. No.: 476,128

[22] Filed: Jun. 7, 1995

[30] Foreign Application Priority Data

Nov. 21, 1994 [DE] Germany .......................... 44 41 315.7
Feb. 16, 1995 [DE] Germany .......................... 195 05 171.8

[51] Int. Cl.$^6$ ..................................... A01N 43/28
[52] U.S. Cl. ..................... 504/154; 504/161; 514/467
[58] Field of Search ............................... 504/154, 295, 504/161; 514/467

[56] References Cited

U.S. PATENT DOCUMENTS

| | | | |
|---|---|---|---|
| 3,690,857 | 9/1972 | Blair | 71/66 |
| 4,851,583 | 7/1989 | Bockowski et al. | 568/465 |
| 5,183,944 | 2/1993 | Werle et al. | 568/465 |

FOREIGN PATENT DOCUMENTS

| | | |
|---|---|---|
| 0066224 | 12/1982 | European Pat. Off. . |
| 4326575 | 2/1995 | Germany . |
| 2079153 | 1/1982 | United Kingdom . |

OTHER PUBLICATIONS

Chemical Abstracts, vol. 73, No. 22, Nov. 30, 1970, 110169.
Chemical Abstracts, vol. 74, No. 22, May 31, 1971, 112779.
Chemical Abstracts, vol. 70, No. 2, Jan. 13, 1969, 4893.

*Primary Examiner*—S. Mark Clardy
*Attorney, Agent, or Firm*—Beveridge, DeGrandi, Weilacher & Young, L.L.P.

[57] ABSTRACT

The direct handling of acrolein for the purpose of combatting microbial, vegetable and animal pests in water and soil is problematic on account of the potential for danger of acrolein. According to the invention a composition which releases acrolein upon contact with water at the site of use and is easy to handle is used.

The composition in accordance with the invention contains an acrolein acetal, preferably 2-vinyl-1,3-dioxolane, and a compound hydrolyzable to an acid with a $pK_s$ value of less than 4, especially one from the series of organic acid anhydrides, organic acid halides and inorganic halogen compounds forming hydrogen halide upon hydrolysis.

22 Claims, No Drawings

METHOD AND COMPOSITION FOR COMBATTING MICROBIAL, VEGETABLE AND ANIMAL PESTS WITH ACROLEIN

INTRODUCTION AND BACKGROUND

The invention relates to a composition which is capable of releasing acrolein and exhibits a biocidal activity by releasing acrolein in the presence of water. The invention also relates to the use of the composition for combatting microbial, vegetable and animal pests as well as to a method of carrying this out.

A large network of irrigation canals is maintained in warm climatic zones with expansive fields and plantations under agricultural use. These canals can be readily clogged by water plants, that is, algae and weeds. The plants hinder the rate of flow in the canals and endanger the smooth functioning of the pump stations necessary for operation. For this reason, it is customary to dope the water in such an irrigation system with a biocide. Acrolein has proven itself in practice as a biocide.

In addition to its as yet unexcelled activity, acrolein also offers the advantage that it degrades in water after a brief time. Thus, acrolein is no longer effective as biocide for irrigating fields but rather is degraded to degradation products harmless to plant physiology. However, the handling of acrolein is very risky due to its physical and chemical properties. Acrolein is poisonous, very toxic upon inhalation, pungent, lachrymatory and readily flammable (flash point −29° C., boiling point 53° C.). Furthermore, there is an explosive polymerization danger due to contamination of the acrolein with impurities.

In view of the risks presented, which result both during transport and in the handling of acrolein, there is a need to perform the doping with a comparably effective biocide which is considerably less risky to handle.

U.S. Pat. No. 4,851,583 teaches the obtention of acrolein which is effective as pesticide by means of the deacetalation of acrolein acetals, also including cyclic acrolein acetals, in the presence of a strongly acidic ion exchanger as catalyst. However, this method is not suitable for the direct doping of flowing water because a rapid contamination or inactivation of the ion exchanger would occur. Furthermore, most acrolein acetals have only a very limited solubility in water and in addition the rate of dissolution is low: For example, approximately 10 minutes are needed to produce a solution of 2-vinyl-1,3-dioxolane (VDL), which is almost saturated under conditions of practice, in water (approximately 8% by weight) under intensive mixing. The factors cited previously make it difficult to use acrolein acetals to release acrolein at the place of need, that is, directly in the irrigation canals, especially since electric energy for intensive mixing is not available there.

Another way of doping water is described in U.S. Pat. No. 5,183,944. Here, acrolein is formed by the deacetalation of acrolein acetals in aqueous phase in the presence of a strongly acidic catalyst. For the doping of aqueous solutions the acrolein formed during the deacetalation in a reaction vessel is constantly removed from the aqueous phase and transferred into the aqueous solution to be doped. This transfer takes place either by means of a current of gas conduced through the reaction vessel, which is subsequently conducted into the aqueous solution to be doped, or by using a liquid-jet pump whose motive agent is the aqueous solution to be doped. This method is suited for doping e.g. cooling-water circuits in industrial systems but can not be used to dope the water in irrigation canals because in general neither electric energy for operating the pumps nor chemically trained professional personnel is available at the doping site.

Unpublished German patent application 43 26 575 teaches a method of doping flowing water which avoids the disadvantages of the direct use of acrolein and is simpler to carry out than previously known methods which method uses an acrolein acetal as biocide precursor. In this method a 25 to 95% by weight solution of an acrolein acetal in an organic solvent and a 3 to 30% by weight aqueous mineral-acid solution are placed at first in a fixed amount ratio into a mixing chamber, the reaction mixture subsequently passed through a specially constructed deacetalation reactor and then transferred into the water to be doped.

Although the method previously evaluated represents a solution of the problem, it nevertheless has a few disadvantages: A special deacetalation reactor and, in addition to a pressure-resistant storage container for the acrolein acetal, one for an aqueous mineral acid are required for carrying out this method, which increases the expense; also, the regulation of the ratio between the acrolein acetal and the aqueous acid by means of perforation blending is not without problems.

Unpublished German patent application P 44 41 315.7 teaches an anhydrous composition which is capable of releasing acrolein and thus suitable for biocide treatment and which contains an acetal of acrolein with an alcohol with 1 to 6 C atoms and 1 to 4 hydroxyl groups and contains an acid with a $pK_s$ value of less than 4 which is at least partially soluble in the acetal and is therewith chemically compatible. However, in as far as the acid is not absolutely anhydrous a discoloration and an undesired rise in the viscosity of the composition can occur after a fairly long storage time.

SUMMARY OF THE INVENTION

The present invention has the problem of indicating a further method with which microbial, vegetable and animal pests can be combatted with acrolein but without having to transport acrolein itself to the site of need and to handle it there. The method should be simple to manage and not dependent on the supply of electric energy, e.g. for operating pumps, agitating and heating devices. A further problem concerns making a composition available which is reliable to use, capable of releasing acrolein and during the use of which the preparation of a second chemical and mixing the latter into the composition at the site of use for the purpose of releasing acrolein is eliminated. Finally, the release of acrolein from the composition should be able to be carried out without the necessity of a special reactor.

The problem is solved by preparing and using a composition containing acrolein acetal and releasing acrolein upon contact with water which is characterized by a content of a compound which releases an acid with a $pK_s$ value of less than 4 by means of hydrolysis.

It was found that a mixture of one or more acrolein acetals and one or more hydrolyzable, acid-forming compounds as defined herein and, to the extent necessary, of auxiliary agents is sufficiently stable in storage in the absence of water, that is, no deacetalation occurs. The composition in accordance with the invention can therefore be transported and stored in moisture-proof barrels and does not exhibit the known handling problems of acrolein. A rapid hydrolysis of the acid-forming compound and, as a consequence thereof, a deacetalation of the acetal and a release of the biocidally active acrolein does not occur until the composition makes contact with water.

DETAILED DESCRIPTION OF INVENTION

The acrolein acetal contained in accordance with the invention in the composition is an open-chain or cyclic acetal comprising no free hydroxyl groups; the basic alcohol component is generally based on a mono- or bivalent alcohol with 1 to 6 C atoms. Monovalent alcohol components of acetal are especially methanol, ethanol, n- and isopropanol and bivalent alcohol components are especially ethylene glycol, 1,2- and 1,3-propylene glycol. In principle, the acetal can also be based on a tri- or tetravalent alcohol component such as glycerol, trimethylolpropane 1,2,6-hexanetriol and pentaerythritol; however, such acetals are difficult to produce without hydroxyl groups. Especially preferred acrolein acetals are those with a 2-vinyl-1,3-dioxolane- or 2-vinyl-1,3-dioxane structure, especially 2-vinyl-1,3-dioxolane and 2-vinyl-1,3-dioxane, which can be easily obtained from acrolein and ethylene glycol or 1,3-propane diol. Acrolein acetals with longer aliphatic groups in the alcohol component are less preferable on account of their low solubility in water.

A number of requirements are placed on the compound contained in the composition and forming acid upon hydrolysis: It must be soluble in sufficient amount in the acrolein acetal or homogeneously emulsified or suspended therein. One or more acids with a $pK_s$ of less than 4 can result upon the hydrolysis of the acid-releasing compound. At least one of the acids released upon hydrolysis must have a $pK_s$ value of less than 4, preferably less than 2.5 and especially less than 2. A hydrolyzable compound from which hydrogen chloride is produced upon hydrolysis is especially preferred. The acid-forming compound and the acrolein acetal must be chemically stable in a mixture with one another in the absence of moisture—this stability is determined by an expert in the art by orienting tests in order to obtain a composition in accordance with the invention which is stable in storage. The acid-forming compound as well as its hydrolysis products should also preferably be environmentally compatible, that is biologically degradable, and as non-toxic as possible.

Among the compounds which can be hydrolyzed under formation of an acid organic acid anhydrides are well-suited under the premise that the $pK_s$ value of the acid is below 4. The following can be named by way of example: Maleic acid anhydride and 2-mono- and 2,3-disubstituted maleic acid anhydride, which substituent(s) is (are) preferably electron-attracting, furthermore, pyromellitic acid mono- or preferably dianhydride.

A further class of hydrolyzable, acid-forming compounds which can be used in accordance with the invention are organic acid halides, especially chlorides, bromides and iodides with acid chlorides being preferred. The organic acid constituting the base of the acid halide can be an aliphatic, cycloaliphatic, aromatic or heterocyclic acid, e.g. a mono-, di-, tri- or polycarboxylic acid, a sulfonic acid or phosphonic acid. Normally, those acid halides are used whose organic group contains 1 to 12 C atoms, preferably 2 to 6 C atoms. The following are cited by way of example: Acetyl chloride, acetyl bromide, acetyl iodide, propionyl chloride, oxalyl chloride, succinyl chloride, adipoyl chloride, benzoyl chloride.

A particularly effective class of hydrolyzable compounds are inorganic halogen compounds which release hydrogen halide, especially HCl, upon hydrolysis. These compounds fall with advantage under the general formulas $MX_m$ or $MOX_{(m-2)}$ or $R_pMX_{(m-p)}$, in which M stands for silicon, titanium, tin, phosphorus, arsenic, antimony or sulfur, R for methyl or ethyl or phenyl and X for Cl, Br or I, especially Cl, and m for the valence of M; m is a whole number between 3 and 5, p a whole number between 1 and 3 and (m-p) is not equal to 0. Even oligomers of the cited substance classes such as e.g. $(X_{m-1}M)_2O$. Especially preferred compounds are silicon tetrachloride and titanium tetrachloride as well as phosphorus oxychloride. In the case of $SiCl_4$ an addition of 0.5 to 5% by weight, especially 1 to 3% by weight, relative to the composition is completely sufficient for a rapid hydrolysis of the acrolein acetal on account of the favorable molecular weight and the high acid strength of the hydrochloric acid formed.

The acrolein acetal or acrolein acetal mixture and the acid-forming, hydrolyzable compound or mixture Of such compounds can be present in the composition in any desired molar ratio; however, the molar ratio is advantageously in a range of 50 to 1 to 1 to 1, especially 50 to 1 to 10 to 1. The higher the concentration of acid-forming compound in the composition is and the higher the acid strength of the acid formed during the hydrolysis, the more rapidly the deacetalation of the acetal occurs after the contacting of the composition with water. The acrolein acetal content in the composition should be as high as possible in order to achieve as high a biocidal effectiveness as possible with a given amount of composition. An especially preferred composition contains a preferred acrolein acetal or mixture of several acetals and contains one or more preferred, acid-forming compounds from the series of acid anhydrides, acid halides and inorganic halogen compounds in a weight ratio in a range of 99.5 to 0.5 to 80 to 20, especially in a range of 98 to 2 to 90 to 10.

The composition in accordance with the invention advantageously contains one or several surfactants which are stable in the presence of the acid-forming compound and of the acrolein acetal. The amount of surfactant added is customarily between 5 and 0.05% relative to the composition but usually an amount between 0.2 to 1% by weight is sufficient. Especially suitable surfactants are ethoxylation products of fatty alcohols, alkyl phenols, fatty acids, fatty amides and glycerol mono- and di-fatty acid esters which are free of hydroxyl groups or exhibit only a low hydroxyl number. The surfactant must be sufficiently stable in storage and soluble in the composition and also be capable of reliably emulsifying the composition after contact with water. In the absence of a surfactant or too low a concentration thereof an separation can occur in the case of slightly water-soluble acrolein acetals, e.g. 2-vinyl-1,3-dioxolane, so that the deacetalation takes place incompletely or in a delayed manner. In the presence of a sufficient amount of an effective surfactant the composition of the invention dissolves in a clear manner within a few seconds and the deacetalation also takes place practically quantitatively at approximately 20° C. within a few minutes.

In addition to the components essential for the invention and the surfactant which is preferably also present in addition the composition can contain other additives in as far as they are stable in the composition. Possible other additives are e.g. other biocides and water-soluble, aprotic, organic solvents.

The compositions of the invention can be produced by simply mixing the components together and are in general clear solutions. The compatibility of the components with each other is assured beforehand by storage tests. The mixing and storing of the composition take place under the exclusion of moisture.

The composition of the invention can be used, since the highly effective biocide acrolein is released upon contact with water, as a means for combatting microbial, vegetable and animal pests. The pests include in particular bacteria and fungi, algae and water weeds, insects, worms and rodents.

In order to combat microbial, vegetable and animal pests with acrolein a composition in accordance with the invention is either (i) brought into direct contact with a medium containing the pests to be combatted or (ii) mixed with water in a weight ratio of 1 to 1 to 1 to 50, preferably 1 to 5 to 1 to 20, and the reaction mixture added directly or after further dilution with water into the medium containing the pests to be combatted after a reaction time which is necessary for an extensive deacetalation of the acrolein acetal contained in the composition.

The ratio of acrolein acetal to water in the method alternative (ii) is advantageously selected so that during the deacetalation a pH of around/below 2 is maintained for a few minutes and only subsequently is the mixture diluted further.

For the purpose of a rapid dissolution of the composition in water the composition is preferably sprayed into water with a single, or better yet, multiple spray jet so that very fine and therefore readily emulsifiable and rapidly soluble droplets result immediately. The spraying in can be effected e.g. using appropriate jet nozzles and a bottle of compressed gas. In method alternative (i) acrolein is released to the moisture content of the medium in a correspondingly slower manner. Method alternative (i) can be used e.g. to combat nematodes or rodents in the ground.

Alternative (ii) is especially suited for combating aquatic pests such as e.g. algae and weeds in irrigation canals. For this, the deacetalated mixture is introduced continuously or periodically in such an amount into the water containing the pests that an acrolein content in a range of 0.1 to 20 ppm acrolein is maintained in it.

Advantages of the composition of the invention are its easy production, good storage capacity and ability to be handled and its ability to be used to combat pests. Since the composition itself contains a precursor of the deacetalation catalyst, such a catalyst does not have to be mixed into an acrolein acetal in dosed form at the site of use. Due to the selected components of the composition neither an expensive device nor a special deacetalation reactor are necessary for being able to release acrolein from the acrolein acetal. The method for combatting bacterial, vegetable and animal pests thus turns out to be simple, requires no electric energy and can be carried out by personnel with little training.

EXAMPLE 1

75.0 g maleic acid anhydride were dissolved under agitation in a mixture of 1417.5 g vinyl-1,3-dioxolane (VDL) and 7.5 g surfactant based on a polyoxyethylene glycerol monooleate (Tegotens® 02 of the Th. Goldschmidt AG company).

a) 100 ml of this solution were charged into 600 ml water; after 6 min the release of acrolein was stopped by neutralization to pH 6. The conversion of the VDL was 97.4% (determined by gas chromatography).

The $pK_s$ value of the maleic acid formed from the anhydride and catalyzing the deacetalation is approximately 1.8.

b) 100 g of a composition according to example 1 were sprayed with a spray jet under a pressure from an $N_2$ bottle of compressed gas of 3 bar into 1000 ml water. The emulsion which formed at first became a clear solution in a few seconds. After 10 minutes dwell time 99.6% of the acrolein bound in the VDL had been released (determination by gas chromatography).

As a result of the addition of the aqueous concentrate containing released acrolein to water containing aquatic pests in a ratio of e.g. 1 to 5000 an acrolein concentration of approximately 10.6 ppm (parts per million) is adjusted, which is suitable for combatting the pests.

EXAMPLE 2

7.5 g acetyl chloride were added under agitation to a mixture of 282.1 g VDL and 1.45 g surfactant (Tegotens® 02). A homogeneous solution was immediately obtained.

16.2 g of this solution were added under agitation to 162 ml water. The reaction was stopped after 6 min. Gas-chromatographic analysis yielded a conversion of 99.7% of the VDL added.

EXAMPLE 3

100 g VDL were mixed with 2.0 g silicon tetrachloride. The mixture is homogeneous and stable in storage.

This mixture was charged under agitation into 600 ml water and the reaction stopped after 5 min by adding sodium hydroxide solution. The conversion rate was 99.5%.

EXAMPLE 4

Method of Preventing Flowing Water from Becoming Clogged with Algae and Weeds The composition in accordance with the invention and according to example 1 is brought to the site of application in a container sealed against moisture and provided with a feed tube. The composition exiting from the feed tube is conducted via a hose into the water to be doped by applying a pressure of 3 bar from an $N_2$ bottle of compressed gas onto the container. In order to obtain the conditions of time and acidity necessary for splitting the acetal the developing solution is only diluted at first to the extent that a pH of approximately 1.5 to 2 is maintained for a time of about 5 to 10 minutes. This takes place e.g. in a helically coiled hose. After sufficient deacetalation the deacetalized, aqueous concentrate containing the acrolein is diluted with an amount of the water to be doped which is sufficient for arriving at the desired application concentration.

A further suitable measure for maintaining optimal deacetalation conditions is to spray the composition of the invention into a container filled with a defined amount of water; this container is itself purposefully located in the water to be doped. After expiration of the dwell time the container is opened and the released acrolein washed into the canal. Alternatively, the composition can be sprayed into a tube (or hose) through which water flows and is located in the water to be doped, which tube allows only a limited amount of water to pass through on account of its length and its cross section, given the extant flow rate, and assures a sufficient dwell time before further diluting.

We claim:

1. A storage stable composition comprising in the absence of water, 80 to 98% by weight premixed acrolein acetal and 2 to 20% by weight of a compound which releases an acid with a $pk_s$ value of less than 4 by means of hydrolysis, and up to 5% by weight surfactant, whereby said acetal will undergo deacetalation to release acrolein upon contact with water.

2. The composition according to claim 1 wherein said compound is selected from the group consisting of an organic acid anhydride, organic acid halide and an inorganic halogen compound forming hydrogen halide upon hydrolysis.

3. The composition according to claim 2, wherein said organic acid anhydride is maleic acid anhydride or pyromellitic acid dianhydride or an acid chloride of a carboxylic acid, phosphonic acid or sulfonic acid.

4. The composition according to claim 2, wherein said acid chloride is a chloride or oxychloride of silicon, titanium, tin, phosphorus or sulfur.

5. The composition according to claim 1, wherein the acrolein acetal is open-chain or cyclic, has no free hydroxyl groups and is based on a mono- or bi-valent alcohol component with 1 to 6 C atoms.

6. The composition according to claim 5, characterized in that it contains 2-vinyl-1,3-dioxolane as acrolein acetal.

7. The composition according to claim 1, characterized in that it contains a surfactant in addition.

8. The composition according to claim 1, characterized in that the $pK_s$ value of the released acid is less than 2.5.

9. The composition according to claim 1, characterized in that it contains the acrolein acetal and the acid-releasing compound in a molar ratio of 50 to 1 to 10 to 1.

10. The composition according to claim 1, characterized in that it contains an essentially hydroxyl-group-free or -poor ethoxylation product of a fatty alcohol, fatty acid, fatty amine or a glycerol mono- or di-fatty acid ester as surfactant.

11. A method of combating microbial, vegetable and animal pests with acrolein, comprising:

selecting a premixed composition in the absence of water containing 80 to 98% by weight acrolein acetal which releases acrolein upon contact with water and 2 to 20% by weight of a compound which releases an acid with a $pk_s$ value of less than 4 when hydrolyzed, and up to 5% by weight surfactant, which composition is chemically stable in the absence of water, contacting said pest by (a) direct contact of said premixed composition with a medium containing said pest, or (b) by mixing said premixed composition with water in a weight ratio of 1 to 1 to 50, and adding the resulting reaction mixture directly or after further dilution with water into a medium containing said pest after a reaction time which is necessary for deacetalation of the acrolein acetal contained in said composition.

12. The method according to claim 11, wherein said acid is a member selected from the group consisting of an organic acid anhydride, an organic acid halide, and an inorganic halogen compound forming hydrogen halide upon hydrolysis.

13. The method according to claim 12, wherein said inorganic halogen compound is a chloride or oxychloride of silicon, titanium, tin, phosphorus, or sulfur.

14. The method according to claim 11, wherein said acid is a member selected from the group consisting of maleic acid anhydride, pyromellitic acid dianhydride, a phosphoric acid ester, a sulfonic acid, an α-halogenated lower carboxylic acid, a sulfuric acid monoalkyl ester and an acid chloride of a carboxylic acid, phosphoric acid or sulfonic acid.

15. The method according to claim 11 wherein the acrolein acetal is open-chain or cyclic, has no free hydroxyl groups and is based on a mono- or bi-valent alcohol component with 1 to 6 C atoms.

16. The method according to claim 15, wherein 2-vinyl-2,3-dioxolane is the acrolein acetal.

17. The method according to claim 11 wherein said composition further contains a surfactant.

18. The method according to claim 11 wherein the $pK_s$ value of the released acid is less than 2.5.

19. The method according to claim 11 wherein the acrolein acetal and the acid-releasing compound are present in a molar ratio of 50 to 1 to 10 to 1.

20. The method according to claim 11 wherein an essentially hydroxyl-group-free or -poor ethoxylation product of a fatty alcohol, fatty acid, fatty amine or a glycerol mono- or di-fatty acid ester is present as surfactant.

21. The method according to claim 11 for preventing the clogging of an aquatic system with algae and weeds, wherein said reaction mixture is introduced continuously or periodically in a sufficient amount into said aquatic system and achieves rapid deacetalation of said acetal after contact of said composition with water so that an acrolein content in a range of 0.1 to 22 ppm acrolein is maintained in said aquatic system.

22. The method according to claim 11 further comprising mixing said premixed composition with water and spraying the resulting formulations into a container containing additional water and placing said container in an aquatic system to be treated for combatting said pest.

* * * * *